United States Patent
Al-Zaydi et al.

(10) Patent No.: US 10,981,872 B1
(45) Date of Patent: Apr. 20, 2021

(54) DI(2-ARYL HYDROZONOPROPANAL) ARENE DERIVATIVES

(71) Applicant: King Abdulaziz University, Jeddah (SA)

(72) Inventors: Khadijah Mohamed Al-Zaydi, Jeddah (SA); Tamer Said Sayed Mohamed Saleh, Jeddah (SA)

(73) Assignee: King Abdulaziz University, Jeddah (SA)

(*) Notice: Subject to any disclaimer, the term of this patent is extended or adjusted under 35 U.S.C. 154(b) by 0 days.

(21) Appl. No.: 17/081,022

(22) Filed: Oct. 27, 2020

(51) Int. Cl.
*C07D 213/53* (2006.01)
*C07C 251/80* (2006.01)

(52) U.S. Cl.
CPC .......... *C07D 213/53* (2013.01); *C07C 251/80* (2013.01)

(58) Field of Classification Search
None
See application file for complete search history.

(56) References Cited

PUBLICATIONS

Mabkhot et al. "Substituted thieno[2,3-b]thiophenes and related congeners: Synthesis, β-glucuronidase inhibition activity, crystal structure, and POM analyses" Bioorganic & Medicinal Chemistry, 2014, vol. 22, No. 23, pp. 6715-6725.*

* cited by examiner

*Primary Examiner* — Joseph R Kosack
(74) *Attorney, Agent, or Firm* — W & C IP

(57) ABSTRACT

Di (2-Aryl Hydrazonopropanal) arene derivatives are provided. The compounds exhibit high levels of toxicity against e.g. human colon cancer cells and are used to treat cancer.

10 Claims, 1 Drawing Sheet

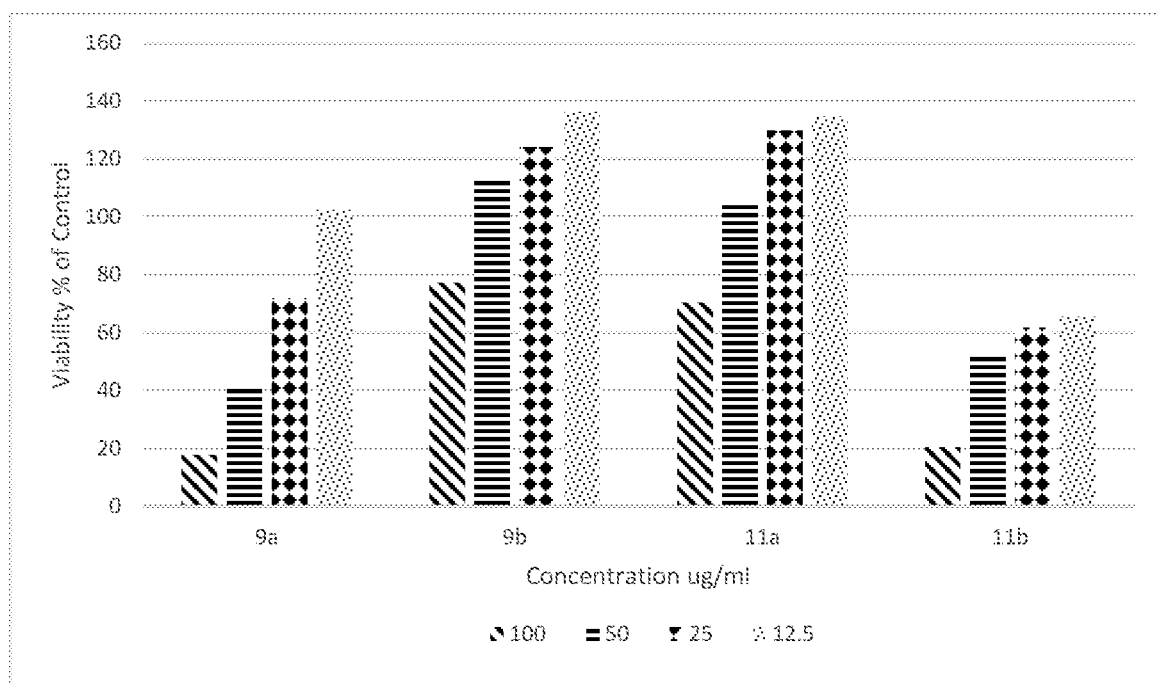

DI(2-ARYL HYDROZONOPROPANAL) ARENE DERIVATIVES

FIELD OF THE INVENTION

The invention generally relates to novel cytotoxic agents for treating cancer. In particular, the invention provides di(2-Aryl Hydrazonopropanal)arene derivatives that exhibit high levels of toxicity against e.g. human colon cancer cells.

BACKGROUND OF THE INVENTION

The American Cancer Society has reported that cancer is the second leading cause of death and is expected to surpass cardiovascular disease in a few years [1]. Colorectal cancer (CRC) is one of the most malignant cancers diagnosed in the gastrointestinal tract (GIT), and requires different staging criteria, adjuvant treatment and operative methods. CRC metastases result in a significant number of cancer related deaths. The molecular mechanisms underlying this complex, multi-step pathway have not been completely elucidated [2]. With the rapid development of resistance to multiple chemotherapeutic agents, the high toxicity of existing drugs and the significant number of side effects associated therewith, there is a need to discover more effective chemotherapeutic agents.

Chemotherapy is crucial for CRC and may be used during a treatment course at different stages including after surgery to kill any remaining cancer cells, or cancer cells that may have escaped from the main tumor and metastasized to other parts of human body. Metastatic cells may not be detected in imaging tests due to their small size. This type of therapy is referred to as adjuvant chemotherapy and the intention is to lower the chance that the cancer will recur. Many chemotherapeutic agents are already used in this stage including fluorouracil (5-FU), Leucovorin (Wellcovorin), irinotecan (Camptosar), and oxaliplatin (Eloxatin). Most adjuvant chemotherapy treatment schedules last for about six to eight months. However, chemotherapy can damage healthy cells along with cancer cells and cause serious side effects such as tiredness (fatigue), nausea and vomiting, diarrhea and abdominal cramping, low white blood cell count, mouth sores (mucositis), bone marrow failure and peripheral neuropathy [5]. Also, sometimes chemotherapy may be used with radiation before surgery to shrink the cancer and facilitate tumor removal. This type of therapy is called "neoadjuvant chemotherapy". Also, in case of metastasis in which cancer has already spread to other organs, chemotherapy is used to reduce problem of tumors, but this is typically an advanced case in which no cure is expected, but the chemotherapy helps patients to feel better and live longer [5].

Cytotoxic compounds that exhibit anti-cancer and anti-metastatic efficacy towards CRC include natural products such as curcumin, which is the active ingredient of turmeric. It is a highly pleiotropic molecule that inhibits cell proliferation and induces apoptosis in cancer cells. Conjugating curcumin to a biodegradable polymer, poly (D, L-lactic-co-glycolic acid), overcomes the photo instability of curcumin. The curcumin-PLGA conjugate efficiently inhibits cell proliferation and cell survival of human colon carcinoma cells (HL116) when compared to native curcumin. Additionally, curcumin conjugated with PLGA shows improved cellular uptake and exhibits controlled release at physiological pH when compared to native curcumin. The curcumin PLGA conjugate efficiently activates the cascade of caspases and promotes intrinsic apoptotic signaling [6].

Unfortunately, such natural compounds still have low therapeutic index. Therefore, the exploration of synthetic compounds for use as cytotoxic agents is important and many reports deal with this issue. For example, two novel series of dimeric 3,5-bis(arylidene)-4-piperidones 1 and 2 have been prepared as cytotoxic agents [7]. These compounds demonstrated potent cytotoxicity against HCT16 and HT29 colon cancer cell lines, exhibiting $IC_{50}$ values in the low micromolar to nanomolar range. Both compounds were more potent than the reference drug 5-fluorouracil which is used in treating colon cancer [7].

Tangeda and Garlapati introduced pyrrolo [2,3-d]pyrimidines with heteroaryl substitutions at the $5^{th}$ position through a sulfur linker, and the compounds exhibited cytotoxic effect towards HCT116 colon cancer cells. Compounds 3 and 4, with nitrobenzimidazole and pyrimidyl heterocycles attached at $5^{th}$ position, were the most potent of all with $IC_{50}$ values of 17.6 mM [8].

Nunes et al. introduced a library of 23 spiropyrazoline oxindoles that show antiproliferative activity towards HCT116 cancer cells [9], and most of this library showed good antiproliferative activity.

The synthesis and cytotoxicity of a series of substituted 6,7-dimethoxyquinazoline derivatives has also been reported. The cytotoxic activity of all the compounds was evaluated against HCT116 colon cancer cells and a HEY ovarian cancer cell line that is naturally resistant to cisplatin. Nine of the tested compounds showed significant cytotoxicity in all cell lines at 10 mM [10]. A structure/activity relationship study for a series of twenty-five substituted 6,7-dimethoxyquinazoline derivatives revealed that the substitution of the hydrogen at position-3 with a lipophilic n-butyl group reduced anti-cancer activity, whereas the introduction of a bulky aromatic group as substituent at position-2 of the quinazoline ring was favorable for cell inhibitory activity [10].

Chemotherapeutic agents play a crucial role in the treatment of CRC. However, the agents with the highest activity also harm normal cells (they are not selective for cancer cells) and cause serious unwanted side effects. There is a need to provide potent novel anti-cancer agents which are more selective for cancer cells and thus have fewer side effects.

SUMMARY OF THE INVENTION

Di(2-aryl hydrazonopropanal)arene-based compounds have been synthesized and shown to be potent cytotoxic agents human cancers, such as colon cancer. The compounds comprise a phenylene or divalent pyridine central core connected on either side to a 2-arylhydrozone-3-oxo-3-substituted propanal group. The disclosed compounds advantageously exhibit good therapeutic indices and high selectivity indices for cancer cells rather than normal cells i.e. they readily kill cancer cells but advantageously display low toxicity for normal, non-cancer cells. Thus, when used to treat cancer, they should cause fewer unwanted side effects than cancer drugs that are currently used.

BRIEF DESCRIPTION OF THE DRAWINGS

FIG. 1. Growth inhibition of HCT 116 cancer cells.

DETAILED DESCRIPTION

Provided herein are compounds of Formula Y—X—Y, where X is aryl or heteroaryl, and Y is

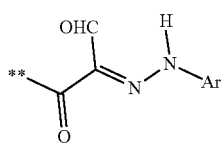

where ** is a point of attachment to X. In the compounds, Ar represents

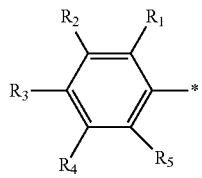

where R1, R2, R3, R4 and R5 are independently the same or different and are H, lower alkyl, or CN, with the caveat that at least one of R1, R2, R3, R4 and R5 is not H; and where * is the point of attachment to the amine group of Y.

In some aspects, Ar is phenyl, o-substituted phenyl, m-substituted phenyl, p-substituted phenyl.

Lower alkyl refers to branched or unbranched alkyl chains having from about 1 to about 10 carbon atoms, e.g. methyl, ethyl, n-propyl, isopropyl, n-butyl, sec-butyl, t-butyl, n-pentyl, n-hexyl, etc. The lower alkyl groups may be branched or unbranched.

In some aspects, one, two, three or four of R1-R5 are H. For example, four of R1-R5 can be H. In some aspects, Ar is

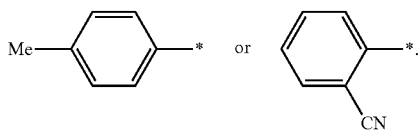

In some embodiments, the compound is a compound represented by Formula I:

Formula I

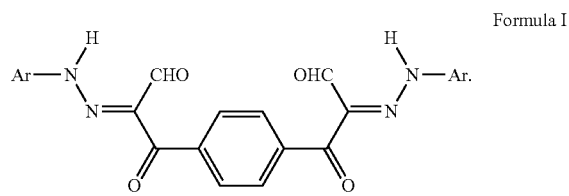

When the compound has a formula represented by Formula 1, Ar can be either

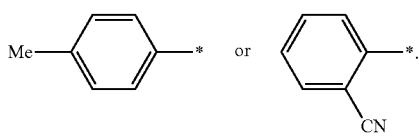

In further aspect, the compound is represented by Formula II:

Formula II

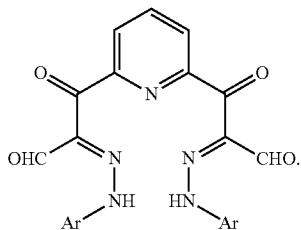

In some embodiments, when the compound is as shown in Formula II, then Ar is

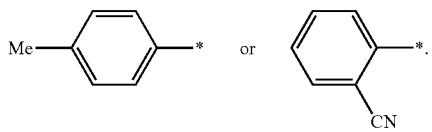

Methods of Making the Compounds

The overall synthetic method involved the coupling of enaminones with diazotized aniline derivatives in the presence of ethanolic sodium acetate to yield the corresponding di aryl hydrazone coupling products.

Generally, a cold (e.g. 25° C.) solution of aryldiazonium salt was prepared by adding a solution of sodium nitrite to a cold equimolar solution of aryl amine hydrochloride (aryl amine in concentrated HCl) with stirring. The resulting solution of the aryldiazonium salt was then added to a cold solution of a dienaminone (e.g. in EtOH) containing sodium acetate, and the mixture was stirred at room temperature for 1 h. A solid product formed and was collected by filtration and then crystallized from an appropriate solvent.

Treatment Methods

Also provided herein are methods of treating cancer (e.g. a tumor and/or malignant cells) in a subject (patient) in need thereof. The methods involve administering to the subject a therapeutically effective amount of one or more of the compounds disclosed herein. In general, a "therapeutically effective amount" is an amount that kills tumor cells, reduces the size of at least one tumor, and/or eliminates the tumor and/or tumor cells. The amount of a compound that is administered is typically in the range of from about 10 to about 1000 mg/kg of body weight, such as about 10, 50, 100, 150, 200, 250, 300, 350, 400, 450, 500, 550, 600, 650, 700, 750, 800, 850, 900, 950 or 1000 mg/body surface area. The amount may vary depending on any of several factors, such as the age, gender, weight, etc. of the patient, the stage of the cancer, etc.

The compounds described herein are generally delivered (administered) as a pharmaceutical composition. Such pharmaceutical compositions generally comprise at least one of the disclosed compounds, i.e. one or more than one (a plurality) of different compounds (e.g. 2 or more such as 2, 3, 4, 5, 6, 7, 8, 9, 10 or more) may be included in a single formulation. Accordingly, the present invention encompasses such formulations/compositions. The compositions generally include one or more substantially purified compounds as described herein, and a pharmacologically suitable (physiologically compatible) carrier, which may be aqueous or oil-based. In some aspects, such compositions are prepared as liquid solutions or suspensions, or as solid forms such as tablets, pills, powders and the like. Solid forms suitable for solution in, or suspension in, liquids prior to administration are also contemplated (e.g. lyophilized forms of the compounds), as are emulsified preparations. In some aspects, the liquid formulations are aqueous or oil-based suspensions or solutions. In some aspects, the active ingredients are mixed with excipients which are pharmaceutically acceptable and compatible with the active ingredients, e.g. pharmaceutically acceptable salts. Suitable excipients include, for example, water, saline, dextrose, glycerol, ethanol and the like, or combinations thereof. In addition, the composition may contain minor amounts of auxiliary substances such as wetting or emulsifying agents, pH buffering agents, preservatives, and the like. If it is desired to administer an oral form of the composition, various thickeners, flavorings, diluents, emulsifiers, dispersing aids or binders and the like are added. The composition of the present invention may contain any such additional ingredients so as to provide the composition in a form suitable for administration. The final amount of compound in the formulations varies but is generally from about 1-99%. Still other suitable formulations for use in the present invention are found, for example in Remington's Pharmaceutical Sciences, 22nd ed. (2012; eds. Allen, Adejarem Desselle and Felton).

Some examples of materials which can serve as pharmaceutically acceptable carriers include, but are not limited to, ion exchangers, alumina, aluminum stearate, lecithin, serum proteins (such as human serum albumin), buffer substances (such as twin 80, phosphates, glycine, sorbic acid, or potassium sorbate), partial glyceride mixtures of saturated vegetable fatty acids, water, salts or electrolytes (such as protamine sulfate, disodium hydrogen phosphate, potassium hydrogen phosphate, sodium chloride, or zinc salts), colloidal silica, magnesium trisilicate, polyvinyl pyrrolidone, polyacrylates, waxes, polyethylene-polyoxypropylene-block polymers, methylcellulose, hydroxypropyl methylcellulose, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, preservatives and antioxidants can also be present in the composition, according to the judgment of the formulator.

"Pharmaceutically acceptable salts" refers to the relatively non-toxic, inorganic and organic acid addition salts, and base addition salts, of compounds of the present invention. These: salts can be prepared in situ during the final isolation and purification of the compounds. In particular, acid addition salts can be prepared by separately reacting the purified compound in its free base form with a suitable organic or inorganic acid and isolating the salt thus formed. Exemplary acid addition salts include the hydrobromide, hydrochloride, sulfate, bisulfate, phosphate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactiobionate, sulfamates, malonates, salicylates, propionates, methylene-bis-.beta.-hydroxynaphthoates, gentisates, isethionates, di-p-toluoyltartrates, methanesulfonates, ethanesulfonates, benzenesulfonates, p-toluenesulfonates, cyclohexylsulfamates and laurylsulfonate salts, and the like. See, for example S. M. Berge, et al., "Pharmaceutical Salts," J. Pharm. Sci., 66, 1-19 (1977) which is incorporated herein by reference. Base addition salts can also be prepared by separately reacting the purified compound in its acid form with a suitable organic or inorganic base and isolating the salt thus formed. Base addition salts include pharmaceutically acceptable metal and amine salts. Suitable metal salts include the sodium, potassium, calcium, barium, zinc, magnesium, and aluminum salts. The sodium and potassium salts are preferred. Suitable inorganic base addition salts are prepared from metal bases which include sodium hydride, sodium hydroxide, potassium hydroxide, calcium hydroxide, aluminum hydroxide, lithium hydroxide, magnesium hydroxide, zinc hydroxide and the like. Suitable amine base addition salts are prepared from amines which have sufficient basicity to form a stable salt, and preferably include those amines which are frequently used in medicinal chemistry because of their low toxicity and acceptability for medical use. ammonia, ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)-aminomethane, tetramethylammonium hydroxide, triethylamine, dibenzylamine, ephenamine, dehydroabietylamine, N-ethylpiperidine, benzylamine, tetramethylammonium, tetraethylammonium, methylamine, dimethylamine, trimethylamine, ethylamine, basic amino acids, e.g., lysine and arginine, and dicyclohexylamine, and the like.

The pharmaceutical preparations may be administered in vivo by any suitable route including but not limited to: by injection (e.g. intravenous, intraperitoneal, intramuscular, subcutaneous, intraarticular, intramammary, intratumoral and the like), and by absorption through epithelial or mucocutaneous linings (e.g., nasal, oral, vaginal, rectal, gastrointestinal mucosa, and the like and/or by e.g. implantation of a delivery device that is implanted in the vicinity of a tumor. In preferred embodiments, the mode of administration is intravenous.

In addition, the compositions may be administered in conjunction with other treatment modalities such as substances that boost the immune system, various chemotherapeutic agents, antinausea agents, pain medication, radiation, surgical resection, and the like. In particular, administration may be performed in conjunction with radiation and/or surgery and the compounds may be used for adjuvant and/or neoadjuvant chemotherapy.

Types of cancer that can be treated include but are not limited to: Acute Lymphoblastic Leukemia (ALL), Acute Myeloid Leukemia (AML), Adrenocortical Carcinoma, AIDS-Related Cancers, Kaposi Sarcoma, AIDS-Related Lymphoma, Primary CNS Lymphoma, Anal Cancer, Appendix Cancer, Astrocytomas, Atypical Teratoid/Rhabdoid Tumor, Central Nervous System, Basal Cell Carcinoma, Bile Duct Cancer, Bladder Cancer, Bone Cancer, Ewing Sarcoma Family of Tumors, Osteosarcoma and Malignant Fibrous Histiocytoma, Brain Stem Glioma, Brain Tumor (e.g. Astrocytomas, Brain and Spinal Cord Tumors, Brain Stem Glioma, Central Nervous System Atypical Teratoid/Rhabdoid Tumor, Central Nervous System Embryonal Tumors, Central Nervous System Germ Cell Tumors, Craniopharyngioma, Ependymoma), Breast Cancer, Bronchial Tumors, Burkitt Lymphoma, Carcinoid Tumor, Gastrointestinal, Cardiac (Heart) Tumors, Central Nervous System (e.g. Atypical Teratoid/Rhabdoid Tumors, Embryonal Tumors, Germ Cell Tumors, Lymphomas), Cervical Cancer, Childhood Cancers, Cholangiocarcinoma, Chordoma, Chronic Lymphocytic Leukemia (CLL), Chronic Myelogenous Leukemia (CML), Chronic Myeloproliferative Neoplasms, Colon Cancer, Colorectal Cancer, Craniopharyngioma, Cutaneous T-Cell Lymphoma, Ductal Carcinoma In Situ (DCIS), Embryonal Tumors, Endometrial Cancer, Ependymoma, Esophageal Cancer, Esthesioneuroblastoma, Ewing Sarcoma, Extracranial Germ Cell Tumo, Extragonadal Germ Cell Tumor, Eye Cancer, Intraocular Melanoma, Retinoblastoma, Fallopian Tube Cancer, Fibrous Histiocytoma of Bone, Malignant, and Osteosarcoma, Gallbladder Cancer, Gastric (Stomach) Cancer, Gastrointestinal Carcinoid Tumor, Gastrointestinal Stromal Tumors (GIST), Hairy Cell Leukemia, Head and Neck Cancer, Heart Cancer, Hepatocellular (Liver) Cancer, Histiocytosis, Langerhans Cell, Hodgkin Lymphoma, Hypopharyngeal Cancer, Intraocular Melanoma, Islet Cell Tumors, Pancreatic Neuroendocrine Tumors, Kaposi Sarcoma, Kidney (Renal Cell, Wilms Tumor and Other Childhood Kidney Tumors), Langerhans Cell Histiocytosis, Laryngeal Cancer, Leukemia (Acute Lymphoblastic (ALL), Acute Myeloid (AML), Chronic Lymphocytic (CLL), Chronic Myelogenous (CML), Hairy Cell), Lip and Oral Cavity Cancer, Liver Cancer (Primary), Lung Cancer (Non-Small Cell, Small Cell), Lymphoma, Macroglobulinemia, Waldenström—see Non-Hodgkin Lymphoma, Malignant Fibrous Histiocytoma of Bone and Osteosarcoma Melanoma, Intraocular (Eye), Merkel Cell Carcinoma, Mesothelioma, Malignant, Metastatic Squamous Neck Cancer with Occult PrimaryMouth Cancer, Multiple Endocrine Neoplasia Syndromes, Multiple Myeloma/Plasma Cell Neoplasm, Mycosis Fungoides, Myelodysplastic Syndromes, Myelodysplastic/Myeloproliferative Neoplasms, Myelogenous Leukemia, Chronic (CML), Myeloid Leukemia, Acute (AML), Myeloma, Multiple, Myeloproliferative Neoplasms, Chronic, Nasal Cavity and Paranasal Sinus Cancer, Nasopharyngeal Cancer, Neuroblastoma, Non-Hodgkin Lymphoma, Oral Cancer, Oral Cavity Cancer, Lip and Oropharyngeal Cancer, Osteosarcoma and Malignant Fibrous Histiocytoma of Bone, Ovarian Cancer, Epithelial, Germ Cell Tumor, Low Malignant Potential Tumor, Pancreatic Cancer, Pancreatic Neuroendocrine Tumors (Islet Cell Tumors), Papillomatosis, Paraganglioma, Paranasal Sinus and Nasal Cavity Cancer, Parathyroid Cancer, Penile Cancer, Pharyngeal Cancer, Pheochromocytoma, Pituitary Tumor, Plasma Cell Neoplasm/Multiple Myeloma, Pleuropulmonary Blastoma, Primary Central Nervous System (CNS) Lymphoma, Primary Peritoneal Cancer, Prostate Cancer, Rectal Cancer, Renal Cell (Kidney) Cancer, Renal Pelvis and Ureter, Transitional Cell Cancer, Retinoblastoma, Rhabdomyosarcoma, Salivary Gland Cancer, Sarcoma (Ewing, Kaposi, Osteosarcoma, Rhabdomyosarcoma, Soft Tissue, Uterine), Sézary Syndrome, Skin Cancer, Small Intestine Cancer, Squamous Cell Carcinoma, Squamous Neck Cancer with Occult Primary, Metastatic Stomach (Gastric) Cancer, T-Cell Lymphoma, Cutaneous, Testicular Cancer Throat Cancer, Thymoma and Thymic Carcinoma, Thyroid Cancer, Ureter and Renal Pelvis, Transitional Cell Cancer, Urethral Cancer, Uterine Cancer, Vaginal Cancer, Vulvar Cancer, and Wilms Tumor.

In some aspects, the cancer is colon cancer.

The cancer may be a primary tumor or may be a secondary (metastatic) tumor, or a subject may have both primary and metastatic tumors that need to be treated.

Also provided are methods of killing a cancer cell or cancer cells. The method involves contacting the cancer cell/cells with an amount of at least one compound as disclosed herein, the amount being sufficient to kill the cancer cell. By "killing" a cancer cell, we mean that the cell and/or components thereof is/are destroyed to the point that the cancer cell can no longer undergo mitosis or migrate, i.e. the cell cannot divide and cannot metastasize. The cancer cell may be in vitro or in vivo. In some aspects, the cancer cell is a colon cancer cell, although the killing of cells of any type of cancer disclosed herein is also encompassed.

It is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Representative illustrative methods and materials are herein described; methods and materials similar or equivalent to those described herein can also be used in the practice or testing of the present invention.

All publications and patents cited in this specification are herein incorporated by reference as if each individual publication or patent were specifically and individually indicated to be incorporated by reference, and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual dates of public availability and may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as support for the recitation in the claims of such exclusive terminology as "solely," "only" and the like in connection with the recitation of claim elements, or use of a "negative" limitations, such as "wherein [a particular feature or element] is absent", or "except for [a particular feature or element]", or "wherein [a particular feature or element] is not present (included, etc.) . . . ".

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

The invention is further described by the following non-limiting examples which further illustrate the invention, and are not intended, nor should they be interpreted to, limit the scope of the invention.

EXAMPLES

Example 1

Novel di(2-aryl hydrazonopropanal)arene derivatives as depicted in Scheme 1 and Scheme 2 were synthesized. Briefly, the enaminones 7,10 required were synthesized previously according to the reported literature [12,13]. Enaminones 7,10 were coupled with diazotized aniline derivatives 8a,b in the presence of ethanolic sodium acetate to yield the corresponding di aryl hydrazone coupling products 9a,b and 11a,b. (Scheme 1 and 2).

Scheme 1

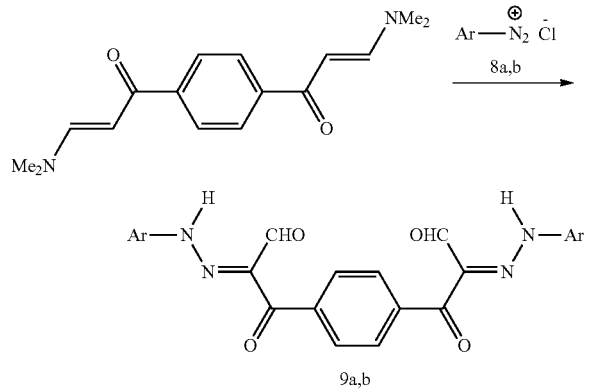

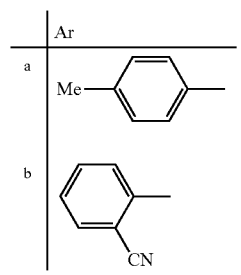

Scheme 2

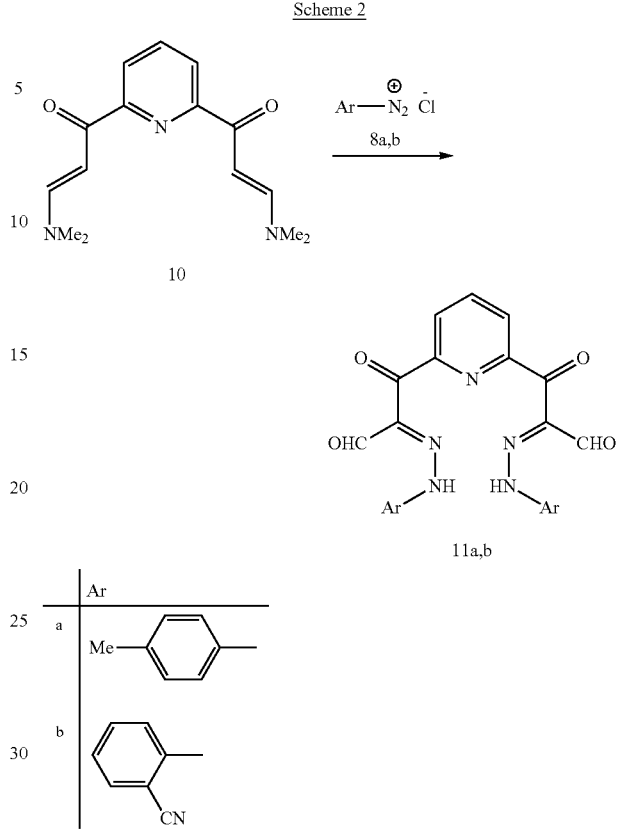

Material and Methods

Synthesis of di (2-arylhydrazone-3-oxo-3-substituted-propanals) Compounds 9a,b and 11a,b A cold solution of aryldiazonium salt 20 mmol was prepared by adding a solution of sodium nitrite (1 g in 10 ml $H_2O$) to a cold solution of aryl amine hydrochloride (20 mmol of aryl amine in 10 ml concentrated HCl) with stirring. The resulting solution of the aryldiazonium salt was then added to a cold solution of dienaminone in EtOH (50 ml) containing sodium acetate (2 g in 10 ml $H_2O$). The mixture was stirred at room temperature for 1 h and the solid product thus formed was collected by filtration and crystallized from the appropriate solvent.

Analysis of Compounds

The configurations of the final products 9a,b and 11a,b were confirmed on the basis of elemental analysis and spectral data that included FT-IR, Mass spectrometry and NMR. The results were as follows:

3-oxo-3-(4-(E)-3-oxo-2-(2-(p-tolyl)hydraziney-lidene)propanoyl)phenyl)-2-(2-(p-tolyl)hydraziney-lidene)propanal (9a)

IR (KBr, v, cm$^{-1}$): 3210 (NH), 2743 (CH), 1715 (CO), 1696 (CO). H NMR (DMSO-$d_6$, 400 MHz): 2.21 (s, 6H, 2CH$_3$), 7.32 (d, 4H, J=8.2 Hz, ArH), 7.41 (d, 4H, J=8.2 Hz, ArH), 7.95 (s, 4H, ArH), 9.78 (s, 2H, 2CHO), 12.54 (s, 2H,

2NH, exchanged with D$_2$O); $^{13}$C NMR (DMSO, 100 MHz): 19.8, 116.3, 127.8, 129.3, 130.2, 136.3, 139.8, 139.9, 186.3, 193.1; MS (m/z): 454 (M$^+$).

2-(2-((E)-1-(4-((Z)-2-(2-(2-cyanophenyl)hydraziney-lidene)-3-oxopropanoyl) phenyl)-1,3-dioxopropan-2-ylidene)hydrazineyl)benzonitrile (9b)

IR (KBr, v, cm$^{-1}$): 3216 (NH), 2743 (CH), 2123 (C≡N), 1711 (CO), 1703 (CO). H NMR (DMSO-d$_6$, 400 MHz): 6.92-7.06 (m, 4H, ArH), 7.33-7.38 (m, 4H, ArH), 8.01 (s, 4H, ArH), 9.91 (s, 2H, 2CHO), 11.19 (s, 2H, 2NH, exchanged with D$_2$O); $^{13}$C NMR (DMSO, 100 MHz): 101.3, 114.5, 116.8, 120.9, 129.4, 133.0, 134.2, 134.8, 140.3, 141.6, 188.1, 195.3; MS (m/z): 476 (M$^+$).

(2E,2'E)-3,3'-(pyridine-2,6-diyl)bis(3-oxo-2-(2-(p-tolyl)hydrazineylidene)propanal) (11a)

IR (KBr, v, cm$^{-1}$): 3301 (NH), 2722 (CH), 1709 (CO), 1695 (CO), 1599 (C=N). $^1$H NMR (DMSO-d$_6$, 400 MHz): 2.23 (s, 6H, 2CH$_3$), 7.41 (d, 4H, J=8.2 Hz, ArH), 7.48 (d, 4H, J=8.2 Hz, ArH), 8.12 (t, 1H, pyridine-H), 8.69 (d, 2H, pyridine —H), 9.58 (s, 2H, 2CHO), 12.95 (s, 2H, 2NH, exchanged with D$_2$O); $^{13}$C NMR (DMSO, 100 MHz): 20.1, 115.9, 123.4, 128.6, 132.1, 133.9, 137.1, 139.0, 143.9, 155.2, 191.3, 196.2; MS (m/z): 455 (M$^+$).

2,2'-(((2E,2'E)-pyridine-2,6-diylbis(1,3-dioxopropan-1-yl-2-ylidene))bis(hydrazin-1-yl-2-ylidene)) dibenzonitrile (11b)

IR (KBr, v, cm$^{-1}$): 3305 (NH), 2734 (CH), 2110 (C≡N), 1713 (CO), 1705 (CO), 1601 (C=N). $^1$H NMR (DMSO-d$_6$, 400 MHz): 7.11-7.16 (m, 4H, ArH), 7.39-7.43 (m, 4H, ArH), 8.23 (t, 1H, pyridine-H), 8.87 (d, 2H, pyridine-H), 9.78 (s, 2H, 2CHO), 11.58 (s, 2H, 2NH, exchanged with D$_2$O); $^{13}$C NMR (DMSO, 100 MHz): 100.9, 114.2, 117.4, 122.1, 125.0, 133.6, 133.9, 134.5, 139.8, 143.2, 156.0, 193.6, 195.0; MS (m/z): 477 (M$^+$).

Cell Culture

Human alveolar basal epithelial cell line (A-549) and human colon carcinoma (HCT-116), purchased from ATCC, USA, were used to evaluate the anticancer properties of the compounds. Cells were routinely cultured in RPMI (Roswell Park Memorial Institute Medium), except HCT-116 cells which were cultured in McCoy's medium. All media were supplemented with 10% fetal bovine serum (FBS), 2 mM L-glutamine, 100 units/ml penicillin G sodium, 100 units/ml streptomycin sulphate, and 250 ng/ml amphotericin B. Cells were maintained at sub-confluency at 37° C. in humidified air containing 5% CO$_2$. For sub-culturing, monolayer cells were harvested after trypsin/EDTA treatment at 37° C. Cells were used when confluence had reached 75%. Tested samples were dissolved in dimethyl sulphoxide (DMSO), and then diluted in the assay to begin with the indicated concentration. All cell culture material was obtained from Cambrex BioScience (Copenhagen, Denmark). All chemicals were from Sigma/Aldrich, USA, unless otherwise indicated. All experiments were repeated three times, unless otherwise indicated.

Anti-Tumor Activity

Cytotoxicity of tested samples was measured against different cancer cells using the MTT Cell Viability Assay. The 3-[4,5-dimethylthiazole-2-yl]-2,5-diphenyltetrazolium bromide (MTT) assay is based on the ability of an active mitochondrial dehydrogenase enzyme of living cells to cleave the tetrazolium rings of the yellow MTT and form dark blue insoluble formazan crystals which are largely impermeable to cell membranes, resulting in its accumulation within healthy cells. Dissolution of the cells results in the liberation of crystals, which are then solubilized. The number of viable cells is directly proportional to the level of soluble formazan dark blue color. The extent of the reduction of MTT was quantified by measuring the absorbance at 570 nm [14].

Reagent Preparation:

MTT solution: 5 mg/ml of MTT in 0.9% NaCl.

Acidified isopropanol: 0.04 N HCl in absolute isopropanol.

Procedure:

Cells (0.5×10$^5$ cells/well), in serum-free media, were plated in a flat bottom 96-well microplate, and treated with 20 μl of different concentrations of the tested samples for 48 h at 37° C., in a humidified 5% CO$_2$ atmosphere. After incubation, media was removed and 40 μl MTT solution/well were added and the cells were incubated for an additional 4 h. MTT crystals were solubilized by adding 180 μl of acidified isopropanol/well and plates were kept at room temperature, followed by photometric determination of the absorbance at 570 nm using a microplate ELISA reader. Triplicate repeats were performed for each concentration and the average was calculated. Data were expressed as the percentage of relative viability compared with the untreated cells compared with the vehicle control, with cytotoxicity indicated by <100% relative viability Calculation:

The percentage of relative viability was calculated using the following equation:

[Absorbance of treated cells/Absorbance of control cells]×100

Then the half maximal inhibitory concentration (IC$_{50}$) was calculated from the equation of the concentration vs % of viability curve.

Results and Discussion

The cytotoxicity of di(2-Aryl Hydrazonopropanal)arene derivatives 9a,b and 11a,b were evaluated in human colon carcinoma HCT-116 cells to determine their toxicity and inhibitory concentrations (IC$_{50}$) using MTT assays. The screened di(2-Aryl Hydrazonopropanal)arene derivatives 9a,b and 11a,b IC$_{50}$ values were compared with the well-known anticancer drug Doxorubicin (DOX) (Table 1). The results from the independent MTT assay revealed that all the di(2-Aryl Hydrazonopropanal)arene derivatives 9a,b and 11a,b were able to inhibit the growth of HCT 116 cancer cells in a dose-dependent manner (FIG. 1). In addition, Table 1 shows the IC$_{50}$ values of the di(2-Aryl Hydrazonopropanal)arene derivatives. As can be seen, compound 11b exhibited an IC$_{50}$ values of 0.09797±0.03 μM for HCT116 cancer cells.

The cytotoxicity of compound 11b was further screened against the normal human alveolar basal epithelial cell line (A-549) (non-tumorigenic) versus HCT116 cell lines as a positive cancer cell line control. The known anticancer drug palladium complex 1 was also tested for comparison. The palladium complex 1 exhibited an IC$_{50}$>37.05±2.9 μM against normal human alveolar basal epithelial cell line (A-549). Compound 11b exhibited a sigmoidal dose-response inhibition of cancer cell viability and had good IC$_{50}$ values. Furthermore, the data indicated that compound 11b exhibited only weak cytotoxic effects on the normal, non-tumorigenic A-549 cell line, compared to the tumor cell line HCT116. This compound thus has an excellent selectivity index.

TABLE 1

IC$_{50}$ of the di(2-Aryl Hydrazonopropanal)arene derivatives 9a,b and 11a,b against the colon cancer cell line HCT 116

| Compound | IC50 (uM) |
|---|---|
| 9a | 0.12623 |
| 9b | 0.2990 |
| 11a | 0.2771 |
| 11b | 0.09797 |
| Doxorubicin | 0.125739 |

While the invention has been described in terms of its several exemplary embodiments, those skilled in the art will recognize that the invention can be practiced with modification within the spirit and scope of the appended claims. Accordingly, the present invention should not be limited to the embodiments as described above but should further include all modifications and equivalents thereof within the spirit and scope of the description provided herein.

REFERENCES

1. Jemal A, Siegel R, Ward E, et al. Cancer statistics, 2006. C A Cancer J Clin 2006; 56:106.
2. Tamas K, Walenkamp A M, de Vries E G, van Vugt M A, Beets-Tan R G, van Etten B, de Groot D J, Hospers G A: Rectal and colon cancer: Not just a different anatomic site. Cancer Treat Rev 2015; 41:671-679.
3. Al-Zaydi K. M., Saleh T. S., Mahdy E. N., El-nagdi M. H. (2019). Antimicrobial and cytotoxic compounds and methods for treating cancer, a bacterial infection, and/or a fungal infection, K. M. Alzaydi, U.S. Pat. No. 10,266,510B2.
4. Al-Zaydi K. M., Saleh T. S., Bin Hadda T. (2019) Potent cytotoxic agents against Human hepatocellular carcinoma cell line based 2-Aryl Hydrazonopropanals Pharmacophore, U.S. Pat. No. 10,280,134B1
5. Van der Jeught K, Xu H-C, Li Y-J, Lu X-B, Ji G., World J Gastroenterol. 2018 24(34): 3834-3848.
6. B. N. Waghela, A. Sharma, S. Dhumale, S. M. Pandey, C. Pathak, PLoS ONE, 2015, 10(2): e0117526. doi:10.1371/journal.pone.0117526
7. S. Das, U. Das, D. Michel, D. K. J. Gorecki, J. R. Dimmock, European Journal of Medicinal Chemistry, 2013, 64, Pages 321-328
8. S. J. Tangeda, A. Garlapati, European Journal of Medicinal Chemistry 45 (2010) 1453-1458.
9. R. C. Nunes, C. J. A. R. Â. Monteiro, C. M. P. Rodrigues, J. D. Amaral, M. M. M. Santos, European Journal of Medicinal Chemistry, 139, 2017, 168-179.
10. M. R. Yadav, F. Grande, B. S. Chouhan, P. P. Naik, R. Giridhar, A. Garofalo, N. Neamati, European Journal of Medicinal Chemistry 48 (2012) 231-243.
11. K. M. Alzaydi, T. S. Saleh, Medicinal Chemistry Research, Medicinal Chemistry Research 29, pages 199-205(2020).
12. Al-Shiekh, M. A.; El-Din, A. M. S., Hafez, E. A.; Elnagdi, M. H., Journal of Chemical Research, 2004, 174-179.
13. A-K Pleier, H. Glas, M. Grosche, P. Sirsch, W. R. Thiel, Synthesis 2001; 2001(1): 0055-0062.
14. Hansen M B, Nielsen S E and Berg K: J. Immunol. Methods 1989; 119:203-10.

We claim:
1. A compound of Y—X—Y, where X is aryl or heteroaryl, and Y is

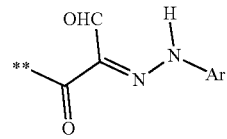

where ** is a point of attachment to X; and wherein Ar is

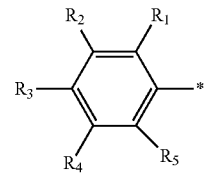

where R1, R2, R3, R4 and R5 are independently the same or different and are H, lower alkyl, or CN, with the caveat that at least one of R1, R2, R3, R4 and R5 is not H; and where * is the point of attachment to the amine of Y.

2. The compound of claim 1, wherein the compound is:

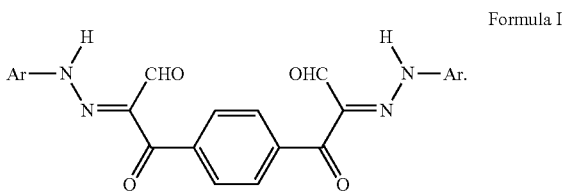

Formula I

3. The compound of claim 2, wherein Ar is

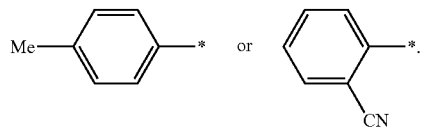

4. The compound of claim 1, where the compound is

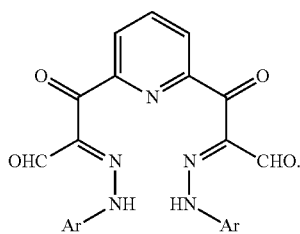

5. The compound of claim 4, wherein Ar is

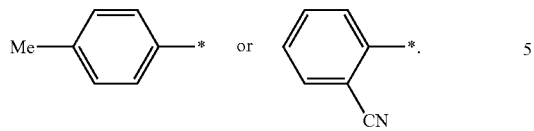

6. A method of treating cancer in a subject in need thereof, comprising
   administering to the subject a therapeutically effective amount of the compound of claim 1.
7. The method of claim 6, wherein the cancer is colon cancer.
8. The method of claim 6, wherein the step of administering is performed with radiation before surgical resection of a tumor.
9. The method of claim 6, wherein the cancer is metastatic cancer.
10. A method of killing a cancer cell, comprising
    contacting the cancer cell with an amount of the compound of claim 1 that is sufficient to kill the cancer cell.

\* \* \* \* \*